(12) United States Patent
Ten Kate

(10) Patent No.: US 9,898,182 B2
(45) Date of Patent: Feb. 20, 2018

(54) GESTURE CONTROL FOR MONITORING VITAL BODY SIGNS

(75) Inventor: Warner Ten Kate, Waalre (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 620 days.

(21) Appl. No.: 13/994,147

(22) PCT Filed: Dec. 14, 2011

(86) PCT No.: PCT/IB2011/055667
§ 371 (c)(1),
(2), (4) Date: Jun. 14, 2013

(87) PCT Pub. No.: WO2012/080964
PCT Pub. Date: Jun. 21, 2012

(65) Prior Publication Data
US 2013/0261771 A1    Oct. 3, 2013

(30) Foreign Application Priority Data
Dec. 17, 2010 (EP) .................................. 10195664

(51) Int. Cl.
*G06F 3/0487* (2013.01)
*A61B 5/00* (2006.01)
*G06F 3/0346* (2013.01)

(52) U.S. Cl.
CPC .......... *G06F 3/0487* (2013.01); *A61B 5/6801* (2013.01); *A61B 5/7475* (2013.01); *G06F 3/0346* (2013.01); *A61B 2560/0266* (2013.01)

(58) Field of Classification Search
CPC .............................. G05B 19/416; G05B 15/02
(Continued)

(56) References Cited

U.S. PATENT DOCUMENTS 4,786,782 A * 11/1988 Takai .................... F24H 9/2014
392/487
5,144,568 A * 9/1992 Glover ............... H03H 17/0263
708/202
(Continued)

FOREIGN PATENT DOCUMENTS

EP    1988492 A1    5/2008
EP    2214093 A1    4/2010
(Continued)

OTHER PUBLICATIONS

AN2768 Application Note, "LIS331DL 3-Axis Digital MEMS Accelerometer: Translates Finer Taps Into Action", Rev. 1, www.st.com, Jun. 2008, pp. 1-17.
(Continued)

*Primary Examiner* — Sean Shechtman

(57) ABSTRACT

The present invention reuses an accelerometer, or, more precise, sensed accelerations of a body sensor for user control of the body sensor. This is achieved by detecting predefined patterns in the acceleration signals that are unrelated to other movements of the patient. These include tapping on/with the sensor, shaking, and turning the sensor. New procedures are described that make it possible to re-use the acceleration sensing for reliable gesture detection without introducing many false positives due to non-gesture movements like respiration, heart beat, walking, etc.

19 Claims, 2 Drawing Sheets

(58) Field of Classification Search
USPC .......................................................... 700/63
See application file for complete search history.

(56) References Cited

U.S. PATENT DOCUMENTS

| | | | |
|---|---|---|---|
| 5,589,887 A | 12/1996 | Wischermann | |
| 5,796,183 A * | 8/1998 | Hourmand | H03K 17/962 307/116 |
| 6,499,043 B1 * | 12/2002 | Forcier | G06F 3/0488 715/273 |
| 7,456,638 B2 * | 11/2008 | Bhansali | G01C 13/008 324/446 |
| 7,647,195 B1 * | 1/2010 | Kahn | A63F 13/10 702/127 |
| 7,650,017 B2 * | 1/2010 | Yamada | G06K 9/00248 345/156 |
| 7,753,861 B1 | 7/2010 | Kahn et al. | |
| 8,111,243 B2 * | 2/2012 | Peng | G06F 3/044 345/173 |
| 8,230,367 B2 * | 7/2012 | Bell | G06F 3/011 382/154 |
| 8,326,569 B2 * | 12/2012 | Lee | G06F 3/017 702/141 |
| 8,463,238 B2 * | 6/2013 | Forstall | H04W 4/001 370/338 |
| 8,547,326 B2 * | 10/2013 | Dods | G06F 1/1626 345/156 |
| 8,564,546 B1 * | 10/2013 | Birch | G06F 3/0416 178/18.01 |
| 8,677,285 B2 * | 3/2014 | Tsern | G04G 21/08 715/702 |
| 2003/0136587 A1 | 7/2003 | Boulet | |
| 2007/0137462 A1 | 6/2007 | Barros et al. | |
| 2007/0208544 A1 * | 9/2007 | Kulach | A61B 5/112 702/189 |
| 2008/0136587 A1 * | 6/2008 | Orr | G08C 19/00 340/5.31 |
| 2008/0150905 A1 | 6/2008 | Grivna et al. | |
| 2009/0295713 A1 * | 12/2009 | Piot | G06F 3/0346 345/156 |
| 2010/0013768 A1 | 1/2010 | Leung | |
| 2010/0208118 A1 | 8/2010 | Ueyama | |

FOREIGN PATENT DOCUMENTS

| | | |
|---|---|---|
| JP | H08111814 A | 4/1996 |
| JP | 2010009498 A | 1/2010 |
| WO | 2010047932 A1 | 4/2010 |

OTHER PUBLICATIONS

Astola et al, "Fundamentals of Nonlinear Digital Filtering", Chapter 3.20 Data-Dependent Filters, 1997 by CRC Press LLC, p. 191-193.

Astola et al, "Fundamentals of Nonlinear Digital Filtering", Non Linear Signal Processing, Chapter 1.1.3.4 Linear Versus Nonlinear Filtering, 1997 by CRC Press LLC, p. 18.

Chen et al, "Amobile Phone-Based Wearable Vital Signs Monitoring System", IEEE, The Fifth International Converence on Computer and Information Technology, 2005, pp. 1-6

Bannach et al, "Rapid Prototyping of Activity Recognition Application", Activity-Based Computing, Pervasive Computing, Publihsed by the IEEE CS, pp. 22-31.

Patently Apple, Celebrating Appl's Spirit of Invention, "Apple Reveals Advanced Sports Monitoring and Head Gesturing Systems", Posted by Jack Purcher on Apr. 16, 2009, 6 Pages.

Sorger, "Alternative User Interfaces" Vienna University of Technology, Undated, pp. 1-11.

"International Support of a Common Awareness & Knowledge Platform for Studying & Enabling Independent Living" www.capsil.org, Undated pp. 1-276.

Troster, "The Agenda of Wearable Healthcare", Imia Yearbook of Medical Informatics, Review Paper, 2005, pp. 125-138.

Hwant et al, "Adaptive Median Filters: New Algorithms and Results", IEEE Transactions on Image Processing, vol. 4, No. 4, Apr. 1995, pp. 499-502.

* cited by examiner

GESTURE CONTROL FOR MONITORING VITAL BODY SIGNS

FIELD OF THE INVENTION

The invention relates to an apparatus and method for controlling operation of body sensors used for monitoring vital body signs.

BACKGROUND OF THE INVENTION

With the advances in embedded microcontrollers, inexpensive miniature sensors, and wireless networking technologies, there has been a growing interest in using wireless sensor networks in medical applications. For example, wireless sensor networks can replace expensive and cumbersome wired devices for pre-hospital and ambulatory emergency care when real-time and continuous monitoring of vital signs is needed. Moreover, body sensor networks can be formed by placing low-power wireless devices on or around the body, enabling long-term monitoring of physiological data.

Personal Emergency Response Systems (PERS) are provided, where a user can use a button (PHB—Personal Help Button) to call for assistance. After the button has been pressed, a wireless telephone connection takes care that the help center of the PERS service operator can assist the user. Recently, a fall detector, i.e. wireless sensor which may include an accelerometer, has been added to the PHB, so that calls for help can be made without the need for an explicit button press.

Furthermore, for elderly patients and people with chronic diseases, an in-house wireless sensor network allows convenient collection of medical data while they are staying at home, thus reducing the burden of hospital stay. The collected data can be passed onto the Internet through a PDA, a cell-phone, or a home computer. The care givers thus have remote access to the patient's health status, facilitating long-term rehabilitation and early detection of certain physical diseases. If there are abnormal changes in the patient status, caregivers can be notified in a timely manner, and immediate treatment can be provided.

Vitals signs like respiration rate and heart rate can be monitored by a new generation of sensors which use wireless connectivity and make use of novel sensing principles. An example of a novel sensing principle is the use of inertial sensors (such as accelerometers, for example) to sense respiration rate, heart rate or other vital signs. In general, inertial measurement components sense either translational acceleration or angular rate. The advances in micro-electromechanical systems (MEMS) and other micro-fabrication techniques have greatly reduced the cost and the size of these devices, and they can be easily embedded into wireless and mobile platforms. Gyroscopes and accelerometers are two common inertial sensors that can be used to capture human motion continuously. The wireless connectivity provides more comfort to the patient and simplifies the operational usage. The sensor can be attached below the clothing of the patient, for patient convenience. However, this makes it cumbersome for the physician to operate the sensor: physically, to find the sensor and knob, but socially, to reach below the clothes. What's more, for hygienic reasons, the sensors are preferably completely sealed and free of knobs. This poses the problem of user control. Using the wireless connection may solve, but leaves the problem of initiating the connection. Power consumption constraints prohibit the radio to be switched on continuously to scan for potential commands.

The use of inertial sensors, such as accelerometers, for detection and classification of human gestures introduces the problem of the reliable distinction between user control commands (gestures) and other motions (movements by the patient as they occur in daily life). For example, in Application Note AN2768: "LIS331 DL 3-axis digital MEMS accelerometer: translates finger taps into actions" by ST, June 2008, a tap detection procedure is described. The procedure is based on sensing the acceleration and identifying a tap when the signal surpasses a certain threshold, while returning below the threshold within a prescribed time window. In a similar way, double taps are detected, by observing a pair of threshold crossings within a prescribed period where each crossing is of a prescribed duration. Although threshold crossing and timing are essential features for detecting a tap, they are not sufficient to obtain reliable detection, in the sense of a low rate of false positives (non-tapping movements that induce a similar signal that will pass the detection procedure) acceptable for practical use. For example, upon heal strike during walking the acceleration signals can show peaks of short duration, and, hence, can trigger the detection of a "tap".

SUMMARY OF THE INVENTION

It is an object of the present invention to provide a more reliable distinction between user control commands (gestures) and other motions in inertial based sensors and to enable simplified user control with no or less knobs, buttons or the like.

This object is achieved by an apparatus as claimed in claim 1, by a body sensor device as claimed in claim 9, by a method as claimed in claim 10, and by a computer program product as claimed in claim 15.

Accordingly, sensed accelerations of a body sensor are used for user control of the body sensor, which is realized by detecting predefined gesture patterns in the acceleration output or signals, that are unrelated to the other movements by the patient. These may include tapping on/with the sensor, shaking, and turning the sensor. Of particular interest are those types of motions that can be performed while the sensor stays attached to the patient, possibly below the clothing. Now, instead of pushing the PHB button the user may also apply a predetermined gesture, e.g., shake the device, in order to get a call connection for help. As another option, the above mentioned PERS fall detector can be extended for vital sign monitoring as described above, or other quantities like stability of gait.

Another advantage of the proposed gesture control is "ease of use" or simplicity. As an example, a nurse does not need to search in an inconvenient manner for the button on the device, particularly if the sensor device is below the pajama of a patient. Moreover, an elderly person in immediate need for help doesn't need to search for a button and just needs to shake the sensor device. Additionally, the sensor device does not need a button any longer and can be cleaned more easily. According to a first aspect, the predetermined gesture may be a tap gesture, wherein the gesture detector is adapted to obtain at least one one-dimensional signal component from the acceleration output, to estimate a background level and to detect a candidate tap if the one-dimensional signal component surpasses a first threshold and the background level is below a second threshold.

As an option of the first aspect, the gesture detector may be adapted to pre-filter the acceleration output to obtain said one-dimensional signal component, and to determine a tap detection event if the candidate tap appears in a predetermined sequence. The pre-filtering may be adapted to select one component of the three-dimensional acceleration output, e.g. the one perpendicular to the patient's body. As another option, the acceleration output can be one-dimensional already (i.e. just a one-dimensional acceleration sensor is used in the sensor device).

Thus, a new algorithm is described that makes it possible to re-use the acceleration sensing for reliable tap detection without introducing many false positives due to non-tap movements like respiration, heart beat, walking, or the like or accidental sensor movements, e.g. bumping against an obstacle, and dropping the sensor.

In the above first aspect, the gesture detector may optionally be adapted to pre-filter the acceleration output by using a complementary median filter. Thereby, small peaks in the acceleration signal can be well detected. Furthermore, according to another option, the gesture detector may be adapted to estimate the background level by using an adaptive median filter. This ensures that false alarms are suppressed at the edges of signals of longer duration. Moreover, according to another option, the gesture detector may be adapted to detect the candidate tap by testing the maximum of the background level to be above a third threshold. Thereby, accidental bumps do not lead to false alarms.

According to a second aspect which can be combined with the first aspect, the predetermined gesture may be a turn gesture, wherein the gesture detector is adapted to analyze acceleration samples of the acceleration output on a frame by frame basis, to determine a reference vector within a frame, and to detect a turn gesture if an angle between the reference vector and a series of acceleration samples is within range from a first threshold for at least a first predetermined number of samples and thereafter below a second threshold for at least a second predetermined number of samples and thereafter within a third threshold for a third predetermined number of samples, which happens before a total duration of a fourth predetermined number of samples. Thereby, turn gestures can be reliably detected and discriminated from other gestures.

According to a third aspect which can be combined with at least one of the first and second aspects, the predetermined gesture may be a shake gesture, wherein the gesture detector is adapted to observe each of three acceleration output components of a three-dimensional acceleration output of the inertial sensor, to compare the acceleration components with predetermined positive and negative thresholds, and to determine a shake detection event if for at least one of the acceleration components the acceleration crosses the positive threshold and the negative threshold a minimum number of times in alternating order and within a maximum duration. Thereby, shake gestures can be reliably detected and discriminated from other gestures.

In a further aspect of the present invention a computer program for performing noise reduction is provided, wherein the computer program comprises code means for causing the load monitoring apparatus to carry out the steps of the above method, when the computer program is run on a computer controlling the load monitoring apparatus.

The above apparatus may be implemented as a hardware circuit, single chip or chip set which can be mounted to a circuit board of a body sensor. The chip or chip set may comprises a processor which is controlled by program or software routine.

It shall be understood that a preferred embodiment of the invention can also be any combination of the dependent claims with the respective independent claim. These and other aspects of the invention will be apparent from and elucidated with reference to the embodiments described hereinafter.

DETAILED DESCRIPTION OF EMBODIMENTS

In the following embodiments, detection procedures for body sensors are described that make it possible to re-use the acceleration sensing for reliable detection of gestures without introducing many false positives due to non-gesture movements. The approach is that in situations where the event to be detected is rare and where many comparable signals are happening, the detection procedures and detectors are designed for specificity first, i.e. an acceptable False Alarm rate (FA), and maximizes sensitivity as much as possible, i.e. a maximal detection probability (PD).

Basically, the problem is that of confusion. An arbitrary movement may induce a similar signal as the gesture to be detected. The approach, therefore, is to design the detectors and detection procedures for virtually no FA and to prescribe (constrain) the gesture movements that will be accepted. These movements are optimized for the intended usage scenarios and users. As a consequence, the user may need to issue the gesture again. This seems acceptable as long as the need to repeat the gesture is seldom and does not get annoying. Another consequence is the need for some form of feedback that gesture is recognized, e.g. through an light emitting diode (LED) shining through the housing or a small speaker that can emit beeps or similar sounds. Perhaps a little exercising for first time users can be helpful, in which case more detailed feedback on the (non)conformance with the prescribed gesture can be effective.

In the following, detection of different specific gestures is described in connection with three exemplary and non-restrictive embodiments. Each detection procedure is based on the typical characteristics that distinguish the gesture from any other movement or touch of the sensor. The typical characteristic of a tap is a peak of short duration. The typical characteristic of a turn is the direction of gravity moving to opposite direction and back again. The typical characteristic of a shake is a set of alternating extreme accelerations.

Figure 1:
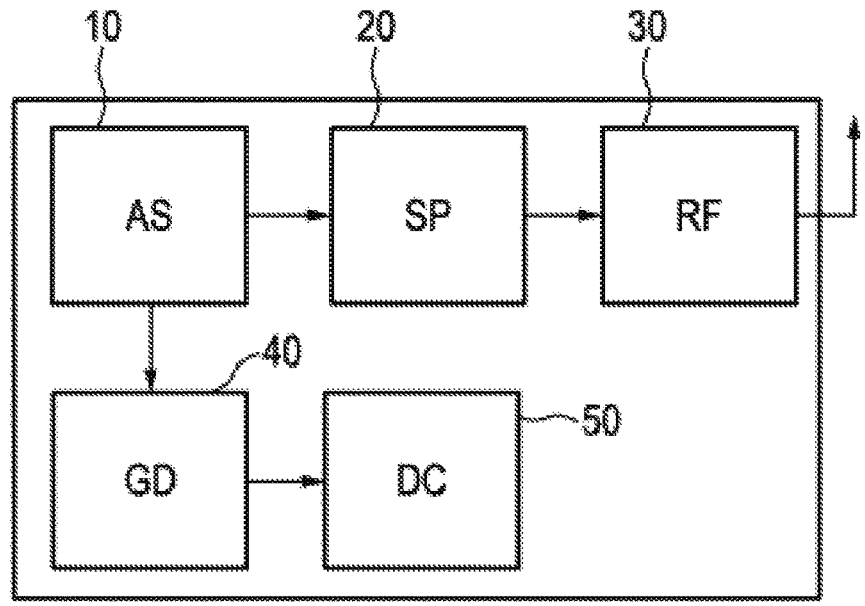
FIG. 1 shows a schematic block diagram of a body sensor in which the detection procedures according to the embodiment can be implemented.

FIG. 1 shows a schematic block diagram of a body sensor in which the detection procedures according to the first to third embodiment can be implemented. The body sensor comprises at least one acceleration sensor 10 or other type of interial sensor for sensing accelerations caused by movements of the body sensor and for outputting an analog or digital three-dimensional (3D) acceleration signal. The output signal of the acceleration sensor (ACC-S) 10 is supplied to a signal processing circuit (SP) 20 which is adapted to detect or filter desired vital body signs to be monitored. The filtered vital body signs are supplied to a radio frequency (RF) front-end 30 in order to be wirelessly transmitted to a remote receiver unit (not shown) via an antenna unit. Of course, the filtered vital body signs could as well be transmitted to the remote receiver unit via a wired transmission.

Furthermore, according to the embodiments, a gesture detector or detection unit (GD) 40 is provided, which receives the output signal of the acceleration sensor 10 (or a filtered version thereof) and processes the received signal so as to detect at least one predetermined gesture which can be used to control the operation of the body sensor. To achieve this, the gesture detection unit 40, which may be a signal processor controlled by a program or software routine to implement a desired detection procedure or algorithm, provides a control input to a sensor control circuit or processor (DC) 50. As an example, the detection of a predetermined gesture, e.g. double tap, may switch on the radio to search for a base station for further communication (data transmission) or control (by means of a user interface (UI) on the base station). The signal processor 20, the gesture detection unit 40 and the sensor control processor 50 may be implemented by a single processor or computer device based on corresponding programs or software routines. In principle, the computation can also be performed outside the device, i.e. the (wireless) connection transmits the raw/partly processed sensor data.

In the following first embodiment, the gesture detection unit 40 of the body sensor of FIG. 1 is provided with a tap detection functionality. The typical characteristic of a tap is a short isolated spike in the acceleration signal. The tapping gesture is defined as double tapping by a finger or the hand against the body sensor. The body sensor is assumed to be attached to a human body, typically the waist. The human body is assumed to be at rest, i.e. not in a motion.

The gesture detector 40 may be adapted to filter accelerometer data from the acceleration sensor 10 to create a signal that emphasizes short peaks. Gestures like tapping are not the only movements that causes short peaks. For example, heel strikes during walking also cause such peaks. Therefore, second characteristics may be that the gesture happens in the absence of other activity, and that the desired gesture is made up of a predetermined sequence of events (e.g. double tap). These characteristics restrict the freedom of use, but considerably improve the rejection of false alarms.

Figure 2:
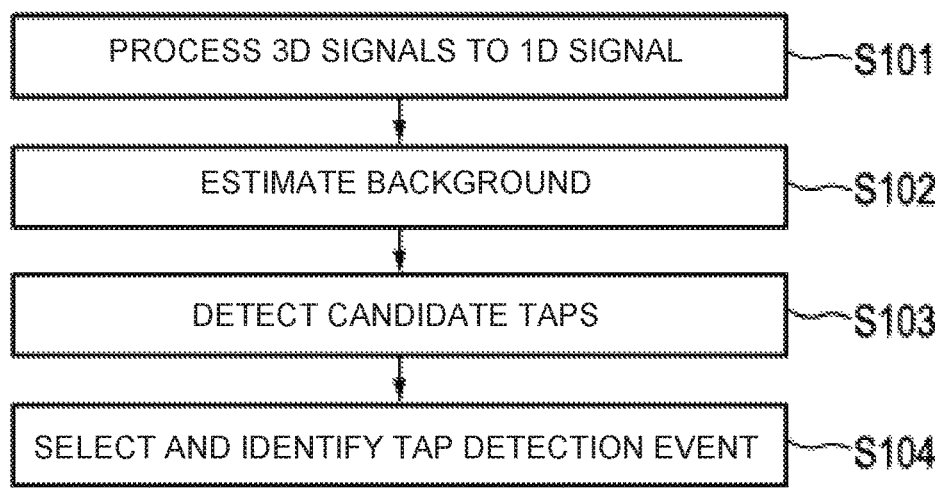
FIG. 2 shows a schematic flow diagram of a tap detection procedure according to a first embodiment.

FIG. 2 shows a schematic flow diagram of the tap detection procedure according to the first embodiment, which comprises the processing steps or blocks of pre-filtering, background level estimation, tap detection and tap selection. The tap detection procedure comprises a pre-filtering step S101, where three-dimensional (3D) acceleration signals of the acceleration sensor(s) 10 are processed into a one-dimensional (1D) signal such that short duration peaks get enhanced. Then, in the subsequent step S102 a background level is estimated from the 1D signal. In a subsequent tap detection step S103, candidate taps are detected if the 1D signal surpasses a threshold, provided that the background level is below another threshold. Then, in the final tap selection step S104, from the remaining taps those that appear in pairs are selected and identified as a tap detection event.

Where traditional tap detection procedures focus on the peak exceeding a threshold, i.e. the sensitivity, the proposed tap detection procedure according to the first embodiment provides specificity by first testing on a low background level. A double tap is required, since single tap like events can still happen in the absence of other activity. An arbitrary design choice is to accept or to reject triple taps. In the exemplary first embodiment, rejection of triple taps has been chosen.

The pre-filtering step S101 makes use of non-linear filters, so as to enhance the short, isolated, spiky character of the taps. A median filter is known to suppress spikes, in other words providing an estimate of the background. The peak itself will not raise the estimate. Vice versa, by applying the median filter in a complementary manner the spikes are found, suppressing the background.

Moreover, depending on the window size the filter is using, the background that will result from a tapping event that is not embedded in further activity can disappear in such a filter, while the background of a movement of longer duration will stay. In this way the background level will initially stay low, but will jump to larger values when the movement takes longer. The estimate in background level obtained in step S102 will rise more than proportionally with duration of the activity, in this way improving specificity. Only spiky movements of short duration can pass the detector, which movements in general are the (double) tap.

More specifically, the pre-filtering in step S101 may consist of a so-called complementary median filter, which is a traditional median filter as described for example in J. Astola and P. Kuosmanen, "Fundamentals of nonlinear digital filtering", CRC Press, 1997, however returning the complement of the filtered signal. The complement is the original value from which the (traditionally) filtered value is subtracted. As an example, a half-window length of 0.5 s may be used. The filter is applied to each of the three components of the 3D acceleration signal. Then, after the filter, the L1 norm of the filtered signals is taken. It was found that this order (first filter, then L1 norm) yielded the most boost of small peaks in the acceleration signal. Also, the L1-norm was found to be more sensitive than the L2-norm, i.e. the L1-norm enhances spikes better than the L2-norm. The L1-norm, also known as the Manhattan distance, is the sum of the absolute values of the vector's components. The L2-norm, also known as the Euclidean distance, is the square root of the sum of squared values of the vector's components.

If implementation costs or other reasons do not leave room, it is expected that the order can be reversed (first norm, then complementary median). In particular at low sampling rates and tapping on a hard surface (e.g., a table), the described order is more sensitive. Another cost saving could be in using only one component (dimension) of the (differentiated) acceleration signal, for example only using the one perpendicular to the user's body.

A way to enhance the spikiness of the signal is to apply the filter on the derivatives of the acceleration signal. The first derivative is known as "jerk", the second as "snap" ("crackle" and "pop" for third and fourth derivates).

However, concerning the estimation of the background level in step S102, described next, experiments revealed differentiation will reduce specificity. The aim is that upon a double tap a low estimate of the background level results, while during any other movement a large estimate results. The ratio between the estimated background level when using differentiation and the background level when using the (undifferentiated) acceleration data indicates that differentiation has the opposite effect to what the aim is. Upon a double tap the ratio is large, while during the walking movement it is low. Hence, as far as estimation of the background level is concerned the (undifferentiated) accelerometer data should be used in step S102.

The principle of the background level step S102 is to suppress tap detection in case of background activity. As already said, the background level is estimated using a second nonlinear filter. It is basically a median filter, so that the spikes themselves get removed. In this way, a fair estimate of the signal background is obtained that quickly follows increments and decrements, while spikes, in particular taps, do not contribute to the estimated level. If the background level estimated in this way surpasses a threshold, the further tap detection is disabled. As an example, a threshold value of 1.2 m/s$^2$ can be used.

A traditional median filter provides an estimate of the background level of a spiky signal. Due to its nonlinear character a low background estimate results in case the signal is of short duration. This is a beneficial effect, since such short signals, if spiky in addition, are most likely due to tapping the sensor. However, at the edges of a signal of longer duration the background estimate will neither rise immediately to the higher level, since the window is largely covering the non-active signal part. This may postpone the suppression of the further tap detection procedure and hence may lead to false alarms.

This problem can be solved by using an adaptive median filter. In such a filter the window length can be adaptively chosen, as described for example in H. Hwang and R. A. Haddad, "Adaptive median filters—new procedures and results", IEEE Trans. Image Proc. 4 (4), 499-502, 1995. Basically, the window size can be adapted depending on the rank order of the median from subsequent subwindows. This is similar to the so-called permutation filter described for example in J. Astola and P. Kuosmanen, "Fundamentals of nonlinear digital filtering", CRC Press, 1997, which also selects an outcome based on the rank order over time. The difference is that the permutation filter selects from subwindows of fixed size, where in the present first embodiment the window size is adapted.

The filter operates as follows. First, the window around the current sample in the signal is split into three subwindows, and the median in each of these subwindows is computed. Then, based on the rank pattern of the three subsequent medians, the following rule base is applied:

If the median computed over the center subwindow is the maximum of the three medians, compute the median over a subwindow of double size to that of the center subwindow.

If the median computed over the center subwindow is the middle between the other two, compute the median over the center subwindow and the subwindow holding the maximum median.

If the median computed over the center subwindow is the minimum of the three medians, use the median of the center subwindow.

As an example, a half window length of 0.2 s can be used for the subwindows. The window length is adapted to improve rising together with an onset, while a low estimate stays in case of an (isolated) tap. In case of an isolated tap the center subwindow will return the largest median, so that the double window length, induced by the rule base, will cause a lower median value, hence further reducing the estimate of the background level. At the onset of a longer activity the three median values will be ranked in the direction of the onset, and the median will be taken over a stronger signal segment, hence yielding a larger estimate of the background level. It is however noted that the above rule base merely provides an example how the window size can be adapted. For example, the doubling in the first rule could, of course, also be any other form of enlarging the window size.

A refinement is to perform some form of averaging over the computed background levels. For example, a power level p could be computed from the obtained background level values b as follows:

$$p=(1/N\Sigma b^2[k])^{1/2},$$

where N is the length of the averaging window.

In case of averaging a simpler estimation of the background level could be used, e.g. a traditional median filter. In the first embodiment, the adaptive median filter can be used without further computation of a power level.

The background power estimation can also be used to control power consumption by the sensor. At high power levels the background activities behave like noise to the sensing measurements and accurate estimations are more difficult. Battery power can be saved by disabling these measurements (until background is low enough).

In the tap detection step S103, those parts of the signal for which the background level was below the associated threshold are tested for peaks exceeding a second threshold. As an example, a threshold value of 7.2 m/s$^2$ can be used.

A peak is the sample with maximum value over a continuous range of samples that are above this second threshold. The range is not strictly continuous in that short drops below the second threshold are permitted. As an example, a maximum drop duration of 0.09 s can be used. For being a tap, the range should be of short duration. This is not tested, however, since in that case the background level will surpass its threshold.

Before accepting the found peak as a tap, an optional third threshold test is performed. In this test the maximum of the background level over the found range is tested to be above a third threshold. As an example, a threshold value of 0.1 m/s$^2$ can be used here. If that maximum in background level is below the third threshold, the tap is rejected. This test is added to enhance specificity (decrease false alarm rate). It was found that when the sensor is lying on the desk (or other solid body, e.g. its charging unit) accidental bumps may cause (double) tap events. Such accidental bumps can happen by slightly lifting the sensor and letting it fall back on the desk (which perhaps happens when taking the sensor out of its charging unit but loosing it to slip back). In those situations the corresponding background level is quite low and less than the situations in which the sensor is held quietly in the hand or attached against the silent human body. The trade-off is a loss of sensitivity for tapping the sensor when it is lying on the desk (or other solid body). It depends on the use scenario whether this is an acceptable trade-off or not.

In the final tap selection step S104, the found taps are tested whether they appear in groups. In the first embodiment only pairs of taps are accepted and cause a detection event. All other group sizes are rejected. A "tap period" is defined as the duration between the two taps of a double tapping event. In informal tests with 16 users showed that the typical distance between the peaks from a double tap is 9 to 17 samples at 50 Hz sampling rate, i.e. 0.18-0.34 s. Thus, as an example, 0.3 s can be used as tap period. Optionally, this value could be made configurable or adaptive.

A tap is considered to belong to a group if it is within a certain duration from the previous tap. As an example, a duration of 1.3 times the above tap period can be used. Before testing whether a tap forms a group with the previous tap, another test is performed, which is called proximity rejection. In this test, if two taps appear too close to each other, one is rejected. This test further improves the specificity, since it is unlikely that a person is tapping that fast. As an example, a duration of 0.3 times the above tap period can be used as boundary duration. In case two taps are considered too close, the tap of smallest magnitude could be rejected. A refinement of this rule could be to consider the distance with the next tap as well. Proximity rejection relates with the drop durations that are permitted in the "continuous" range in the tap detection phase. They cannot be combined in a single test, however.

A tap is detected if a tap group of two taps is found. In the exemplary embodiment, single taps and groups of more than two taps are discarded and do not fire a tap detection. Of course, embodiments with multiple gesture detection units 40 for detecting different gestures (tap groups or other types of gestures) can be provided as well. In an implementation, they can be integrated for optimal load on computational resources and battery power consumption.

In the following second embodiment, the gesture detection unit 40 of the body sensor of FIG. 1 is provided with a turn detection functionality. The turning gesture is defined as holding the sensor in the hand, holding the hand quietly for a short period, quickly fully turning the hand to reversed orientation ("180 degrees"), optionally pause very shortly, quickly turning back, and hold quiet again for a short period. The sensor can be at arbitrary orientation in the hand. The hand is turned around a virtual axis in the (close to) horizontal plane. Typically, the turn is made by turning the wrist or by turning the arm (so that sensor moves upside down and back again). The full turn suggests a 180 degrees rotation of the sensor. Physically, however, it is more of a 90 degrees rotation that happens.

Figure 3:
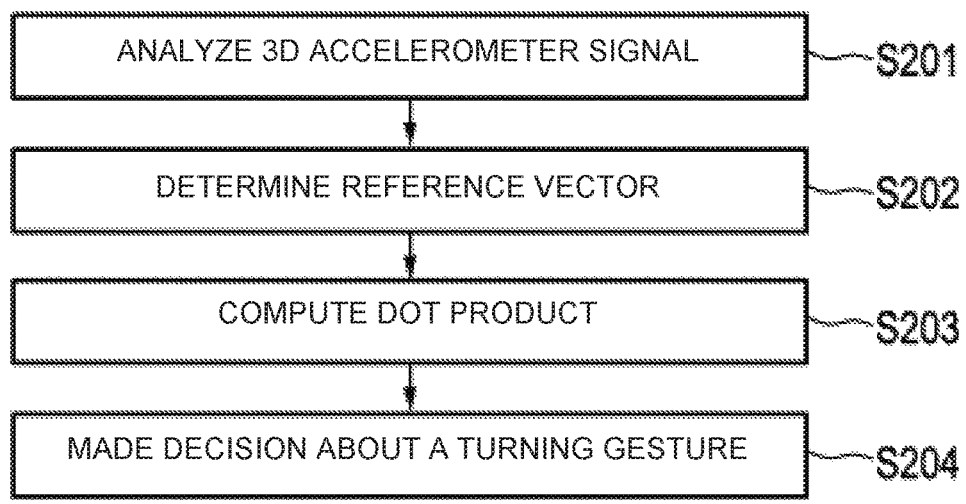
FIG. 3 shows a schematic flow diagram of a turn detection procedure according to a second embodiment.

FIG. 3 shows a schematic flow diagram of the turn detection procedure according to the second embodiment. In step S201 the 3D accelerometer signal is analyzed on a frame per frame basis. In the prototype a frame size of 1.8 s is used. The number of samples to shift to the next frame is dependent on whether a turn, a partial turn, or no turn is detected in the current frame. A partial turn can complete in the next frame. Absence of a turn can in fact include the first holding period. Therefore, when shifting to the next frame at least the number of samples from the potential turn should stay in that next frame.

Then, in step S202 the procedure determines a reference vector. This can be a fixed, predetermined vector, e.g. corresponding to the orientation of the sensor when it is in its usual position (e.g. "upside up"). As another example, this could also be the major acceleration vector within a frame, which is subsequently normalized to unit size. The major acceleration vector is that vector (acceleration sample) to which all others are closest. In other words, the major acceleration vector is the mode in the distribution of acceleration samples. Such a mode can be estimated through a gamma filter, as described for example in J. Astola and P. Kuosmanen, "Fundamentals of nonlinear digital filtering", CRC Press, 1997, where $\gamma \rightarrow 0$. For each sample k in the frame the filter computes the product of the distances of all other samples j to the current sample:

$$\Pi_{j \neq k} |acc[j] - acc[k]|.$$

The sample k for which this product is minimal is selected as the major acceleration vector. Instead of the conventional L2-norm, the L1-norm is used in the second embodiment to compute the distance $|acc[j]-acc[k]|$.

After obtaining the reference vector the dot product z between this vector and each of the other acceleration samples is computed in step S203.

Finally, in step S204 a decision about a turning gesture is made based on predetermined up and down thresholds thresUp and thresDn. A turn is detected in step S204 if the sequence z meets the following pattern:

z>thresUp, for at least upSz0 samples, whereafter
z<thresDn, for at least dnSz samples, whereafter
z>thresUp, for at least upSz1 samples, which happens before a total duration of turnSz samples.

In the prototype we use the following values (the reference vector is of unit size): upSz0=0.36 s, dnSz=0.24 s, upSz1=0.36 s, turnSz=1.8 s, thresUp=8.4 m/s$^2$ (inclination more than 60 degrees "upwards", i.e. in the direction of the major acceleration vector), thresDn=−5.6 m/s$^2$ (inclination more than 30 degrees "downwards"). As an example, the frames may be of the same size as turnSz. A frame is the size of the processing window over which the major acceleration vector is determined.

Experiments indicated the total processing is the fastest, i.e. the computational load is the least, if the frame size is equal to turnSz.

The above exemplary procedure can be generalized as follows. An angle between the reference vector and a series of samples is within a first threshold for a first predetermined number of acceleration samples and thereafter beyond a second threshold for at least a second predetermined number of acceleration samples and thereafter within a third threshold for a third predetermined number of acceleration samples, all within a fourth predetermined number of acceleration samples. Here, "threshold" is to be understood as a range. For example, the angle in the first series is close to zero degrees, i.e. within, for example a range/threshold of ±5 degrees. In the second series the angle is beyond, for example, 90 degrees, i.e. a range of 90 to 180 degrees. In the third series the angle is, for example, again in the range of −5 to 5 degrees.

Two gestures different from turning are known to cause a turn detection, i.e. a FA. They are a full rotation of the sensor, e.g. when tumbling the sensor around in the hand, and shaking the sensor. Therefore, the procedure is optionally extended with additional tests to prevent these FA.

In order to suppress full rotations, it is in addition required that the acceleration vector is in the same half space upon its two crossings (first downwards, then upwards) through the plane perpendicular to the major acceleration vector. This is the case for a back & forth turn, but not for a full rotation around. The test is implemented by computing the dot product of the two acceleration vectors at the moment z changes sign. It is positive (same half space) for a turn, while negative (opposite half spaces) for a full rotation. The test is only performed in case of a "gentle turn" where |acc|, the L2-norm of the sensed acceleration, is close to 1 g, not affected by turning the sensor along a free fall trajectory (causing weak acceleration vectors, and hence unpredictable signs), and neither affected by a fiercefull rotation (causing the acceleration due to gravity to be flooded by centrifugal acceleration, and hence enforcing identical sign for both turn and rotation). A free fall trajectory can happen when turning the sensor through turning the arm. As an example, 4<|acc|<19 can be required for a gentle turn.

It is difficult and therefore unlikely to make a natural motion that fully rotates the sensor along a free fall trajectory within the detection time limit. A fast full rotation is possible to perform fiercefully, but seems to happen only intentionally—just like the turn. The detection time limit requirement, turnSz, poses a limitation on the range of accepted gestures, but is in line with the above explained approach to design the detectors and detection procedures for virtually no FA and to prescribe (constrain) the gesture movements that will be accepted.

By applying a low-pass filter (LPF) on the original 3D acceleration signal, the signal z becomes more "gentle". Indeed, in this way fiercefull rotations could be detected (and suppressed). However, the downward values of z are also smoothed out by the LPF and z<thresDn may not happen anymore, reducing the detection rate. A mixed solution is to detect turns using the unfiltered acceleration signal, while the filtered version is used to identify rotations. Since an LPF increases the computational load, no LPF is applied in the present embodiment. Shaking is suppressed by requiring that during the down phase, z<thresDn must hold contiguously for the dnSz samples. A stronger criterion is to also require that both upwards spans, z>thresUp, are contiguous. Another approach is to detect the (simultaneous) shake, implying the detected turn is a FA. In the second embodiment, only the contiguous down phase may be applied.

In experiments it was found that some users start the turn back movement immediately after the turn forward, i.e. skipping the prescribed pause. Setting dnSz to 0.12 s made the procedure sensitive to those gestures as well. However, it also caused some shakes to be detected as turn. The above measures can counter this reduction in specificity. As already mentioned dnSz=0.24 s may be used.

The computational load can be reduced by omitting the determination of the major acceleration and requiring that the sensor should be held with prescribed orientation. This will also reduce the FA rate, since all other orientations are excluded for detection.

In the following third embodiment, the gesture detection unit 40 of the body sensor of FIG. 1 is provided with a shake detection functionality. The typical characteristic of a shake is a sequence of alternating extreme accelerations. The shake detection procedure is a simple, yet robust procedure.

Figure 4:
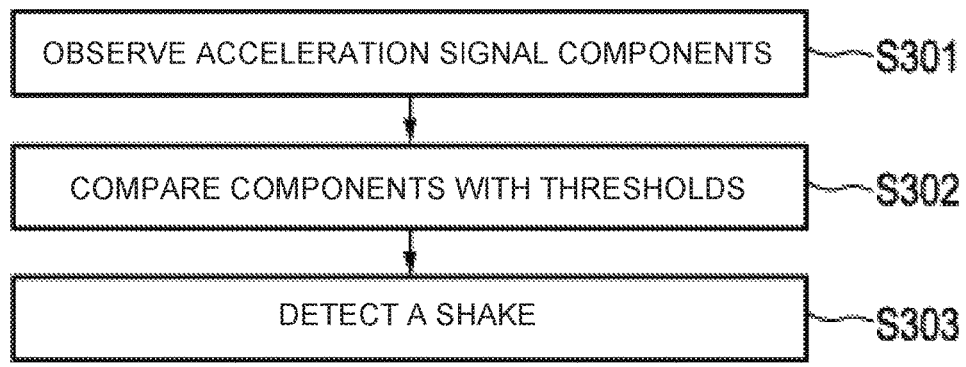
FIG. 4 shows a schematic flow diagram of a shake detection procedure according to a third embodiment.

FIG. 4 shows a schematic flow diagram of the shake detection procedure according to the third embodiment. In step S301 the procedure observes each of the three components of the acceleration signal separately. Then, in step S302 the acceleration components are compared with predetermined positive and negative thresholds. In a final shake decision step S303, a shake is detected, if for at least one of the acceleration components the acceleration crosses the positive threshold and the negative threshold a minimum number of times in alternating order and within a maximum duration. It was found that upon shaking the sensor such a pattern appeared in one or two of the components, depending on the direction in which the sensor is shaked.

As an example, the thresholds can be set to plus and minus 16 m/s$^2$, the minimum number of required crossings can be set to 6, and the maximum duration to 0.9 s. In counting the number of crossings the signal is first monitored for being between the two thresholds. Then, every crossing of a threshold yields a count, provided the threshold being crossed is the alternate from the previous crossing.

In principle, the shake detection procedure of the third embodiment can be adapted to issue its acceleration output in positive numbers only, so that the zero value of the term m/s$^2$ corresponds to a number somewhere in the middle of the output range. Thus, the "positive" and "negative" thresholds may refer to values when the sensor output is or would have been calibrated such that the numbers correspond to a physical acceleration in m/s$^2$.

The present invention can be used in patient monitoring, in particular related to wireless respiration and pulse sensors. The present invention can be applied in other fields as well, in particular, in the contexts of PERS subscribers who wear a pendant or wrist PHB. Pressing the PHB guarantees attention by the call center. It is known that finding the knob at the PHB can be cumbersome to the subscriber in need of help, in particular to frail elderly. Gesture control can replace the need for pressing the button. A high false call rate is, however, not allowed, and a sensitive detection mechanism like the one described, is needed. New generation PHBs (with fall detection) host an accelerometer and processing capacity.

Additionally, energy expenditure through the sensor (accelerometer) worn by the user may be estimated. The estimation uses some "acceleration counts" that are mapped to consumed calories. Since the mapping is different for different activity types an average or most likely mapping is used. As an improvement, the user can control the mapping through gesture control. For example, when starting to bike, a double tap sets the mapping correspondingly. The sensor can stay in the pocket, providing easy control. Again, high sensitivity to discriminate the user command from other movements is needed.

Other variations to the disclosed embodiments can be understood and effected by those skilled in the art in practicing the claimed invention, from a study of the drawings, the disclosure, and the appended claims. In particular, at least two of the above gesture detection procedures of the first to third embodiments can be combined in a single embodiment to provide various control functions triggered by different gestures.

To summarize, the present invention reuses an accelerometer, or, more precise, sensed accelerations of a body sensor for user control of the body sensor. This is achieved by detecting predefined patterns in the acceleration signals that are unrelated to other movements of the patient. These include tapping on/with the sensor, shaking, and turning the sensor. New procedures have been described that make it possible to re-use the acceleration sensing for reliable gesture detection without introducing many false positives due to non-gesture movements like respiration, heart beat, walking, bumping, dropping the device, etc.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

The above steps S101 to S104 of FIG. 2, S201 to S204 of FIG. 3 and S301 to S303 of FIG. 4 can be performed by a single unit or by any other number of different units which not necessarily need to be hosted or mounted in the sensor device. The calculations, processing and/or control of the gesture detection unit 40 of FIG. 1 can be implemented as program code means of a computer program and/or as dedicated hardware.

The computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The present invention reuses an accelerometer, or, more precise, sensed accelerations of a body sensor for user control of the body sensor. This is achieved by detecting predefined patterns in the acceleration signals that are unrelated to other movements of the patient. These include tapping on/with the sensor, shaking, and turning the sensor. New procedures are described that make it possible to re-use the acceleration sensing for reliable gesture detection without introducing many false positives due to non-gesture movements like respiration, heart beat, walking, etc.

The invention claimed is:

1. An apparatus for controlling a sensor device which uses a movement sensor, said apparatus comprising:
    a gesture detector for evaluating an acceleration output of said movement sensor to detect at least one predetermined gesture, wherein the acceleration output is indicative of a movement sensed by the movement sensor; and
    a device controller for controlling a functional operation of said sensor device in response to a detection output of said gesture detector,
    wherein said gesture detector is adapted to perform:
        obtaining two one-dimensional signal components from said acceleration output, including a first one-dimensional signal component and a second one-dimensional signal component, wherein the second one-dimensional signal component is obtained after the first one-dimensional signal component, and the first one-dimensional signal component and the second one-dimensional signal component include a peak indicative of the sensed movement;
        estimating a first background level from the first one-dimensional signal component, wherein the first background level is indicative of a sensed non-tap movement background activity in the first one-dimensional signal component, wherein the sensed non-tap movement background activity is due to a user movement;
        estimating a second background level from the second one-dimensional signal component, wherein the second background level is indicative of the sensed non-tap movement background activity in the second one-dimensional signal component;
        comparing the first one-dimensional signal component with a first threshold, the second one-dimensional signal component with the first threshold, the first background level with a second threshold, and the second background level with the second threshold; and
        detecting a candidate double tap if, based on the comparisons, the first one-dimensional signal component surpasses the first threshold, the second one-dimensional signal component surpasses the first threshold, the first background level is below the second threshold, and the second background level is below the second threshold.

2. The apparatus according to claim 1, wherein said gesture detector is adapted to determine a tap detection event if said candidate double tap appears in sequence.

3. The apparatus according to claim 1, wherein said gesture detector is adapted to pre-filter said acceleration output to enhance peaks indicative of a tap to produce the first one-dimensional signal component and the second one-dimensional signal component.

4. The apparatus according to claim 1, wherein said gesture detector is adapted to filter the first one-dimensional signal component and the second one-dimensional signal component to suppress peaks indicative of a tap to produce the first background level and the second background level.

5. The apparatus according to claim 1, wherein said gesture detector is adapted to detect said candidate double tap by testing a maximum of said first background level to be above a third threshold and a maximum of said second background level to be above the third threshold.

6. A body sensor device comprising:
    an inertial sensor for sensing acceleration of said body sensor device; and
    an apparatus according to claim 1.

7. The apparatus according to claim 1, wherein the device controller controls the sensor device to search for a base station in response to the gesture detector detecting the double tap.

8. The apparatus according to claim 7, wherein the device controller controls the sensor device to transmit data to the base station.

9. The apparatus according to claim 7, wherein the device controller controls the sensor device to receive a control signal from the base station.

10. The apparatus according to claim 1, wherein said gesture detector is adapted to detect a tap gesture by detecting only the candidate double tap.

11. The apparatus according to claim 1, wherein said gesture detector is adapted to reject a single tap as a tap gesture.

12. The apparatus according to claim 1, wherein said gesture detector is adapted to reject a triple tap as a tap gesture.

13. The apparatus according to claim 1, wherein said gesture detector is further adapted to perform:
    observing each of three acceleration components of a three-dimensional acceleration output of said movement sensor, comparing said acceleration components with predetermined positive and negative thresholds, and determining a shake detection event if for at least one of said acceleration components the acceleration crosses said positive threshold and said negative threshold a minimum number of times in alternating order and within a maximum duration; and
    analyzing acceleration samples of said acceleration output on a frame by frame basis, determining a reference vector within a frame, and detecting a turn gesture if an angle between said reference vector and a series of acceleration samples is within a range from a first threshold for at least a first predetermined number of samples and thereafter below a second threshold for at least a second predetermined number of samples and thereafter within a third threshold for a third predetermined number of samples, which happens before a total duration of a fourth predetermined number of samples.

14. The apparatus according to claim 1, wherein said gesture detector estimates at least one the first or the second background levels by averaging over a power level computed from a plurality of obtained background level values.

15. The apparatus according to claim 14, wherein said device controller controls a power consumption of the sensor based on the estimate of the background level.

16. The apparatus according to claim 1, wherein said gesture detector is adapted to accept the candidate double tap only if a distance between a first tap and a second tap of the candidate double tap is less than a predetermined distance.

17. The apparatus according to claim 1, wherein the background activity includes walking.

18. The apparatus according to claim 1, further comprising:
  comparing the first background level with the second threshold; and
  disabling the comparison of the second one-dimensional signal component and the second background level in response to the first background level surpassing the second threshold.

19. The apparatus according to claim 1, wherein the gesture detector is further configured to detect at least one of a shake or a turn.

* * * * *